(12) United States Patent
Covington

(10) Patent No.: US 6,471,660 B1
(45) Date of Patent: Oct. 29, 2002

(54) METHOD AND APPARATUS FOR MEASURING FACTORS IN MAMMARY FLUIDS

(75) Inventor: Chandice Covington, College of Nursing Center for Health Research 5557 Cass Ave., Detroit, MI (US) 48202

(73) Assignee: Chandice Covington, Detroit, MI (US)

( * ) Notice: Subject to any disclaimer, the term of this patent is extended or adjusted under 35 U.S.C. 154(b) by 0 days.

(21) Appl. No.: 09/488,905

(22) Filed: Jan. 21, 2000

Related U.S. Application Data

(60) Provisional application No. 60/116,815, filed on Jan. 21, 1999.

(51) Int. Cl.[7] .................................................. A61B 5/00
(52) U.S. Cl. ........................................ 600/584; 435/7.23
(58) Field of Search ............................ 600/551, 573, 600/584; 604/346, 355; 435/6, 7.23

(56) References Cited

U.S. PATENT DOCUMENTS

| | | |
|---|---|---|
| 3,608,540 A | 9/1971 | Sartorius |
| 3,786,801 A | 1/1974 | Sartorius |
| 3,822,703 A | 7/1974 | Davisson |
| 4,249,481 A | 2/1981 | Adams |
| 4,376,053 A | 3/1983 | Bullock et al. |
| 4,393,811 A | 7/1983 | Bodmin |
| 4,452,779 A | 6/1984 | Cockerill |
| 4,542,750 A | 9/1985 | Ettare |
| 4,583,970 A | 4/1986 | Kirchner |
| 4,680,028 A | 7/1987 | Stuart |
| 4,759,747 A | 7/1988 | Aida et al. |
| 4,761,160 A | 8/1988 | Vermillion |
| 4,883,464 A | 11/1989 | Morifuki |
| 4,941,433 A | 7/1990 | Hanauer |
| 4,964,851 A | 10/1990 | Larsson |
| 5,007,899 A | 4/1991 | Larsson |
| 5,049,126 A | 9/1991 | Larsson |
| 5,071,403 A | 12/1991 | Larsson |
| 5,110,557 A | 5/1992 | Brown et al. |
| 5,476,492 A | 12/1995 | Unrug |
| 5,482,004 A | 1/1996 | Chowdhury |
| 5,493,995 A | 2/1996 | Chowdhurry |
| RE35,316 E | 8/1996 | Negersmith et al. |
| 5,576,329 A | 11/1996 | Hennessey |
| 5,627,034 A | 5/1997 | Gould et al. |
| 5,628,964 A | 5/1997 | Tassitano |
| 5,645,537 A | 7/1997 | Powles et al. |
| 5,664,984 A | 9/1997 | Laughridge |
| 5,720,722 A | 2/1998 | Lockridge |

(List continued on next page.)

FOREIGN PATENT DOCUMENTS

WO    WO 98/22160    5/1998

OTHER PUBLICATIONS

Petrakis, et al. Cholesterol and cholesterol epoxides in nipple aspirates of human breast fluid. Cancer Res. Jun. 1961, vol. 41, pp. 2563–2566.

Patton, et al. Carotenoids of human colostrums. Lipids. 1990, vol. 25, No. 3, pp. 159–165.

Vizoso, et al. Relationship between serum prolactin levels and protein composition of breast secretions in nonlactating women. J. Clin. Endocrinol. Metabol. 1994, vol. 79, No. 2, pp. 525–529.

(List continued on next page.)

*Primary Examiner*—Max Hindenburg
(74) *Attorney, Agent, or Firm*—Knobbe, Martens, Olson, and Bear LLP

(57) ABSTRACT

Provided are methods for non-invasively obtaining mammary fluid from a subject. The method further provides methods for measuring the risk of a mammary disease by measuring a biological factor in the mammary fluid. Further provided is an apparatus useful in obtaining a mammary fluid from the mammary gland of a subject.

37 Claims, 4 Drawing Sheets

U.S. PATENT DOCUMENTS

| | | | |
|---|---|---|---|
| 5,741,649 | A | 4/1998 | Inazawa |
| 5,776,098 | A | 7/1998 | Silver et al. |
| 5,776,177 | A | 7/1998 | MacWhinnie et al. |
| 5,797,875 | A | 8/1998 | Silver |
| 5,798,266 | A | 8/1998 | Quay et al. |
| 5,810,796 | A | 9/1998 | Kimura et al. |
| 5,846,739 | A | 12/1998 | Gould et al. |
| 5,855,889 | A | 1/1999 | Watson et al. |
| 5,885,246 | A | 3/1999 | Ford |
| 5,895,640 | A | 4/1999 | Khalkhali |
| 5,902,267 | A | 5/1999 | Medo |
| 5,902,279 | A | 5/1999 | Powles et al. |
| 5,913,686 | A | 6/1999 | Van Winkle |
| 5,914,238 | A | 6/1999 | Keesee et al. |
| 5,941,847 | A | 8/1999 | Huber et al. |
| 5,922,836 | A | 9/1999 | Watson et al. |
| 6,004,186 | A | 12/1999 | Penny |
| 6,004,756 | A | 12/1999 | Watson et al. |
| 6,063,029 | A | 5/2000 | Saita et al. |
| 6,110,140 | A | 8/2000 | Silver |
| 6,287,521 | B1 | 9/2001 | Quay et al. ................ 422/101 |
| 6,314,315 | B1 | 11/2001 | Hung |
| 6,316,189 | B1 | 11/2001 | Hadded et al. |
| 6,316,215 | B1 | 11/2001 | Adair et al. |
| 2001/0034038 | A1 | 10/2001 | Hung |
| 2001/0039015 | A1 | 11/2001 | Sauter |
| 2002/0002343 | A1 | 1/2002 | Hung et al. |
| 2002/0007115 | A1 | 1/2002 | Hung et al. |
| 2002/0010405 | A1 | 1/2002 | Hung et al. |
| 2002/0013539 | A1 | 1/2002 | Hung |

OTHER PUBLICATIONS

Adami et al., "Absence of association between reproductive variables and the risk of breast cancer in young women in Sweden and Norway," *British Journal of Cancer*, vol. 62, pp. 122–126 1990.

America Cancer Society *Cancer facts and figures*, 1996.

American Cancer Society *Breast cancer facts and figures*, 1996.

Anderson et al., *Cancer*, vol. 65, 1901–1908 1989.

Basu et al., "Serum vitamins A and E, beta–carotene, and selenium in patients with breast cancer," *Journal of the American College of Nutrition*, vol. 8, pp. 524–529 1989.

Bendich et al., "Antioxidant nutrients and immune function," *Advances in Experimental Medicine and Biology*, vol. 262, New York: Plenum Press 1990.

Brisson et al., "Diet, mammographic features of breast tissue, and breast cancer risk," *American Journal of Epidemiology*, vol. 130, pp. 14–24 1989.

Britton et al., *Carotenoids vol. 1a: Isolation and analysis.* Basel: Birkhausen Verlag 1995.

Burton et al., "Antioxidant action of carotenoids," *Journal of Nutrition*, vol. 119, pp. 109–115 1989.

Burton et al., "Beta–carotene: An unusual type of lipid antioxidant," *Science*, vol. 224, pp. 569 1984.

Byers et al., "Dietary carotenes, vitamin C, and vitamin E as protective antioxidants in human cancers," *Annual Review of Nutrition*, vol. 12, pp. 139–159 1992.

Byers et al., "Lactation and breast cancer," *American Journal of Epidemiology*, vol. 121, pp. 139–159 1985.

Dawood et al., *American Journal of Obstetrics and Gynecology*, , 138, 20–24, 1980.

DeLuca, "Vitamin A" In: *The fat–soluble vitamins*, H. Deluca (Ed.), pp. 1–67, New York; Plenum Press. 1978.

Di Mascio et al., "Antioxidant defense systems: The role of carotenoids, tocopherols, and thiols," *American Journal of Clinical Nutrition*, vol. 53, pp. 194–200 1991.

Ewertz et al., "Dietary factors and breast–cancer risk in Denmark," *International Journal of Cancer*, vol. 46, pp. 779–784 1990.

Gaitan et al., *Endocrinology*, Sep, S1(3), 515–520, 1967.

Greiner *Pharmaceutical Tech.*, May 1993, pp. 28–44 1993.

Haagensen et al., *Breast carcinoma: Risk and detection*, Philadelphia: W.B. Saunders Company 1981.

Hill et al., "Retinoids and Cancer Prevention," *Annu. Rev. Nutr.* vol. 12, pp. 161–181 1992.

Hislop et al., "Diet and histologic types of benign breast disease defined by subsequent risk of breast cancer," *American Journal of Epidemiology*, vol. 131, pp. 263–270 1990.

Holmes et al., "Dietary guidelines," In: *Reducing breast cancer in women*, B. Stoll (Ed.), pp. 135–144 1995.

Inaji et al., *Cancer* vol. 60, 3008–3013 1987.

Ing et al., "Unilateral breast feeding and breast cancer," *The Lancet*, vol. 7, pp. 124–127 1977.

Katsouyanni et al., "Risk of breast cancer among Greek women in relation to nutrition intake," *Cancer*, vol. 61, pp. 181–185 1988.

Kinsel et al., *Cancer Res.* 49: 1052–1056, 1989.

Knecht et al., "Serum vitamin A and subsequent risk of cancer: Cancer incidence follow–up of the finish mobile clinic health examination survey," *American Journal of Epidemiology*, vol. 132, pp. 857–870 1990.

Krinsky et al., "Interaction of oxygen and oxy–radicals with carotenoids," *Journal of the National Cancer Institute*, vol. 69, pp. 205 1982.

Krinsky, "Actions of Carotenoids in Biological Systems," *Annu. Rev. Nutr*, vol. 13, pp. 561–587 1993.

Kvale et al., "Lactation and cancer risk: Is there a relationship specific to breast cancer," *Journal of Epidemiology and Community Health*, vol. 42, pp. 30–37 1987.

Layde et al., "The independent association of parity, age at first full–term pregnancy, and duration of breastfeeding with the risk of breast cancer," *Journal of Clinical Epidemiology*, vol. 42, pp. 963–973 1988.

Levin et al., "Lactation and menstral function as related to cancer of the breast," *American Journal of Public Health*, vol. 54, pp. 580 1964.

Love, "Introduction" In: *Reducing breast cancer risk in women*, B. Stoll (Ed.), 1995.

Lubin et al., "Risk factors for breast cancer in women in Northern Alberta Canada as related to age at diagnosis," *Journal of the National Cancer Institute*, vol. 68, pp. 211–217 1992.

MacMahon et al., "Lactation and cancer of the breast: a summary of an international study," *Bulletin of the World Health Organization*, vol. 42, pp. 85 1970.

Marubini et al., "The relationship of dietary intake and serum levels of retinol and beta–carotene with breast cancer," *Cancer*, vol. 61, pp. 173–180 1988.

Matthews–Roth, *Curr. Top. Nutr. Dis.* (*New Prot. Roles Select Nutr.*) vol. 22, pp. 17–38 1989.

Matthews–Roth, *Pure Appl. Chem.* vol. 57, pp. 717–722 1985.

Michnovicz et al., *How to reduce your risk of breast cancer.*, New York: Warner Books 1994.

Mori et al., *Jpn. J. Clin. Oncol.* 19: 373–379 1989.

Negri et al., "Intake of selected micronutrients and the risk of breast cancer," *International Journal of Cancer* vol. 65, pp. 140–144 1995.

Newcomb et al., "Lactatation and a reduced risk of premenopausal breast cancer," *New England Journal of Medicine*, vol. 330, pp. 81–87 1994.

Paganini–Hill et al., "Vitamin A, beta–carotene, and the risk of cancer: A prospective study," *Journal of the National Cancer Institute* vol. 79, pp. 443–448 1987.

Parl et al., *Hum. Pathol.* 19: 960–966, 1988.

Pertschuk et al., *Cancer*, vol. 66, 1663–1670 1990.

Peto et al., *Nature*, vol. 290, pp. 201–208 1981.

Petrakis et al., "Association of breast fluid coloration with age, ethnicity, and cigarette smoking," *Breast Cancer Research and Treatment*, vol. 11, pp. 255–262 1988.

Petrakis et al., "Association of race, age, menopausal status, and cerumen type with breast fluid secretion in non–lactating women as determined by nipple aspiration," *Journal of the National Cancer Institute*, vol. 54, pp. 829–833 1975.

Petrakis et al., "Cerumen phenotype and proliferative epithelium in breast fluids of U.S.–Born immigrant Asian women: A possible genetic–environmental interaction," *Breast Cancer Research and Treatment* vol. 16, pp. 279–285 1990.

Petrakis et al., "Correlation of breast fluid related to concentration of cholesterol, cholesterol epoxides, estrogen, and lipid peroxides," *American Journal of Clinical Pathology*, vol. 89, pp. 117–120 1988.

Petrakis et al., "Nipple aspirate fluids in adult non–lactating women–lactose content, cationic Na+, K+, Na+/K+ ratio, and coloration," *Breast Cancer Research and Treatment*, vol. 13, pp. 71–78 1989.

Petrakis, "Physiologic, biochemical, and cytologic aspects of nipple aspirate fluid," *Breast Cancer Research and Treatments* vol. 8, pp. 7–9 1986.

Pitt "Vitamin A" In: *Fat soluble vitamins: Their biochemistry and applications*, A. Diplock (Ed.), pp. 1–75, London: Heinemann 1985.

Porter–Jordan et al., *Hematol. Oncol. Clin. North Amer.* 8: 73–100 1994.

Potishman et al., "Breast cancer and dietary and plasma concentrations of carotenoids and vitamin A," *American Journal of Clinical Nutrition*, vol. 52, pp. 909–915 1990.

Rohan et al., A population based case–control study of diet and breast cancer in Australia *American Journal of Epidemiology*, vol. 128, pp. 478–489 1988.

Sarhadi et al., *Br J Plast Surg*, (8): 668–670, 1997.

Sartorius "Breast fluid cells help in early cancer detection," *Journal of the American Medical Association*, vol. 224, pp. 823–827 1973.

Sartorius et al., "Cytologic evaluation of breast fluid in the detection of breast disease," *Journal of the National Cancer Institute*, vol. 59, pp. 1073–1078 1977.

Seoud et al., *J. Reprod Med.*, 38(6), 438–442, 1993.

Siskind et al., "Breast cancer and breastfeeding: Results from an Australian case–control study," *American Journal of Epidemiology*, vol. 130, pp. 229–236 1988.

Taylor–Papadimitriou et al., "Cell lineage and interactions in neoplastic expression in the human breast," In: *Understanding Breast Cancer*, M. Rich, J. Hager, & P. Furmanski (Eds.), pp. 215–246, New York: Marcek Dekker, Inc. 1983.

Van't Veer et al., "Dietary fiber, beta–carotene, and breast cancer: Results from a case–control study," *International Journal of Cancer*, vol. 45, pp. 825–828 1990.

Visozo et al., "Factors affecting protein composition of breast secretions from nonlactating women," *Breast Cancer Research*, vol. 23, pp. 251–258 1992.

Wald et al., "Plasma retinol, beta–carotene, and vitamin E. levels in relation to further risk of breast cancer," *British Journal of Cancer*, vol. 49, pp. 321–324 1984.

Weisberger "Nutritional approach to cancer prevention with emphasis on vitamins, antioxidants, and carotenoids," *American Journal of Clinical Nutrition*, vol. 53, pp. 226–237 1991.

Wrensch et al., "Factors associated with obligating nipple aspirate fluid: Analysis of 1428 women and literature reviews," *Breast Cancer Research and Treatment*, vol. 15, pp. 39–51 1990.

Yuan et al., "Risk factors for breast cancer in Chinese women in Shanghai," *Cancer Research*, vol. 48, pp. 1949–1953 1988.

Carotenoids of Human Colostrum, Stuart Patton et al., *Lipids*, vol. 25, No. 3, pp. 159–165 (1990).

Relationship Between Serum Prolactin Levels and Protein Composition of Breast Secretions in Nonlactating Women, Francisco Vizoso et al., *Journal of Clinical Endocrinology and Metabolism*, vol. 79, No. 2, pp. 525–529, 1994.

McTiernan, A., & Thomas, D. (1986). Evidence of a protective effort of lactation on risk of breast cancer in young women. *American Journal of Epidemiology*, 124, 353–358.

Murrell, T. (1991). Epidemiological and biochemical support for a theory on the cause and prevention of breast cancer. *Medical Hypotehses*, 36, 389–396.

Yoo, K–Y., Tajima, K., Kuroishi, T., Hirosi, K., Yoshida, M., Miura, S. & Miura, H. (1992). Independent protective effect of lactation against breast cancer: A cast–control study in Japan. *American Journal of Epidemiology*, 135, 725–733.

Nipple Aspirate Fluid in Epidemiologic Studies of Breast Disease, Nicholas L. Petrakis, *Epidermiologic Reviews*, vol. 15, No. 1, pp. 188–195 (1993).

Exfoliative Cytology of the Human Mammary Gland and Its Value in the Diagnosis of Cancer and Other Diseases of the Breast, George N. Papanicolaou, M.D., Ph.D., et al., *Cancer*, vol. 11, No. 2, pp. 377–409, Mar.–Apr. 1958.

Breast Cancer Incidence in Women with Abnormal Cytology in Nipple Aspirates of Breast Fluid, Margaret R. Wrensch et al., *American Journal of Epidemiology*, vol. 135,, No. 2, 1992.

Mutagenic Activity in Nipple Aspirates of Human Breast Fluid, Nicholas L. Petrakis et al., *Cancer Research*, vol. 40, 188–189.

"Final Results of Ductal Lavage Study Presented AT $23^{rd}$ Annual San Antonio Breast Cancer Symposium: Pre–malignant and Malignant Cells Detected in Women at High–risk for Breast Cancer"; http://www.ductallavage.com/Product/Text/San_Antonio_release.html.

"Lancet Study Shows Promising New Breast Cancer Research Application Using Ductal Lavage" http://www.ductallavage.com/Product/Text/FINALPDHLancetreleased4.26.01htm.

"Study Demonstrates Ductal Lavage Collects Abnormal Breast Cells That Can Help Assess Breast Cancer Risk"; http://www.ductallavage.com/Product/Text/acog.htm; *University Physicians Medical Group*.

IHS® Health Group Midical Industry Today.htm; Study: Ductal Lavage Shows Promise in Breast Cancer Detection.

ER Sauter, et al.; "Nipple aspirate fluid: a promising non–invasive method to identify cellular markers of breast cancer risk"; British Journal of Cancer (1997) 76(4) pp. 494–501.

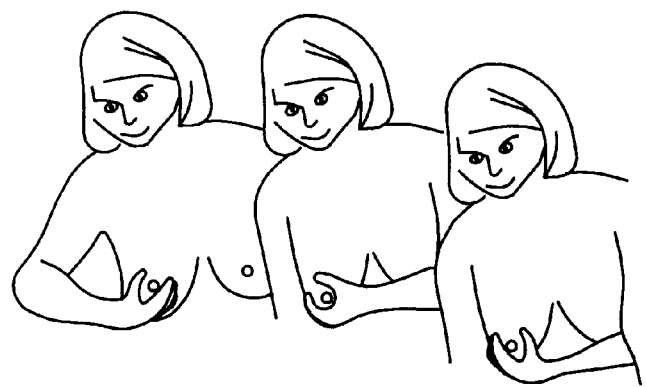
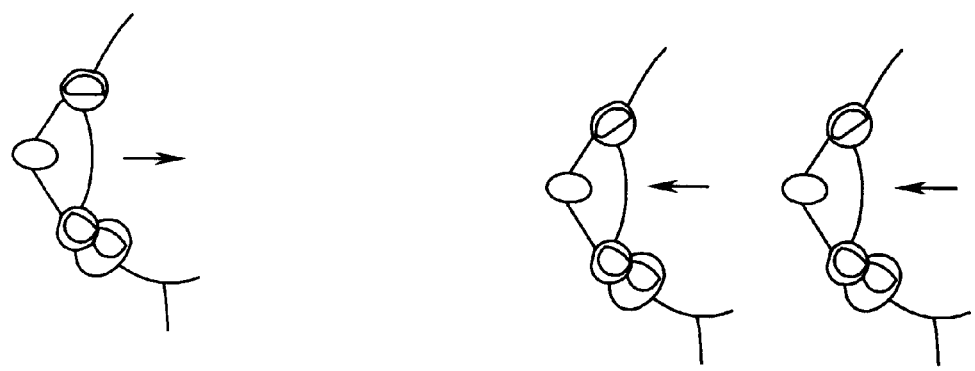
*FIG.2A*
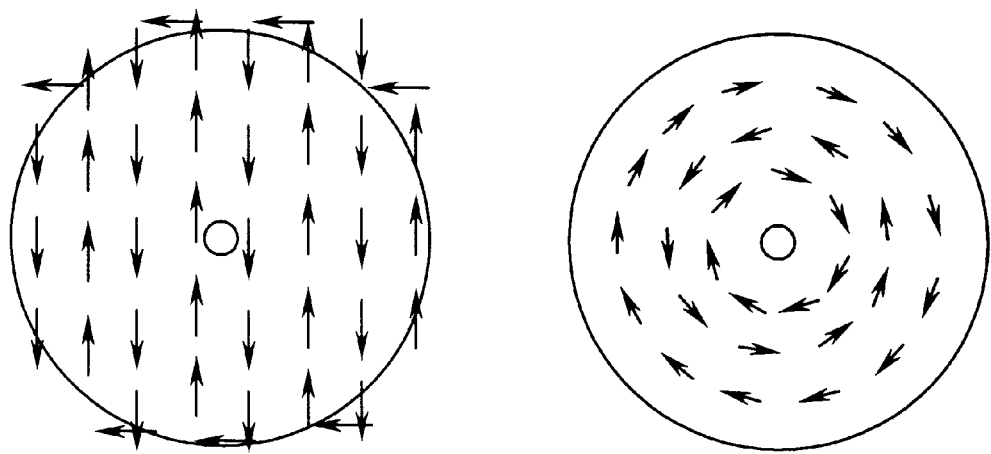
*FIG.2B*

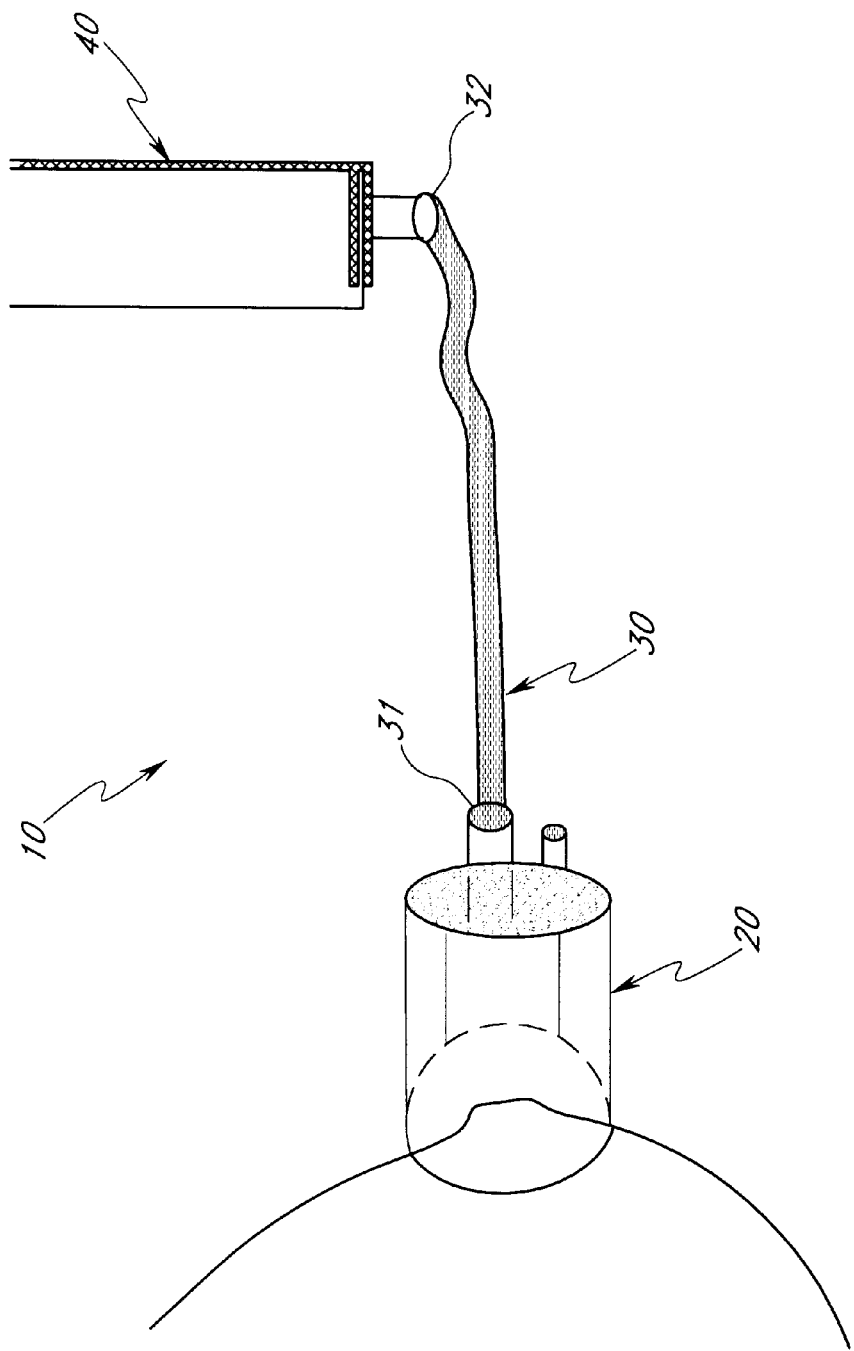

METHOD AND APPARATUS FOR MEASURING FACTORS IN MAMMARY FLUIDS

CROSS REFERENCE TO RELATED APPLICATIONS

This application claims priority from Provisional Application Ser. No. 60/116,815, filed Jan. 21, 1999, to which application a priority claim is made under 35 U.S.C. §119(e).

This invention was made with government support under NIH Grant # NR03142 awarded by the PHS. The government has certain rights in the invention.

FIELD OF THE INVENTION

The present invention relates generally to breast fluid aspirators, and more specifically to an apparatus, a system, and a method for determining the risk of breast disease in a biological sample obtained from the breast by means of a breast fluid aspirator.

BACKGROUND OF THE INVENTION

Breast cancer is one of the leading causes of disease and death in women, with greater than 90% of breast cancer originating in the epithelial cells of the ducts of the breast. Early detection and treatment of breast cancer has focused on improving prognosis and increasing the survival rates. Renewed focus on prevention and detection of breast cancer has lead to the use of numerous biological indicators and methods of early detection of breast cancer risk. Such indicators include numerous oncogenic determinants, cytokines, angiogenic factors, proteins and nucleic acids, as well as biochemical products and lipids.

Carotenoids and retinoids are naturally occurring substances which contain extensively conjugated polyene chains. Carotenoids have extensively conjugated systems of carbon-carbon double bonds which give rise to their many varied and brilliant colors. Many carotenoids and retinoids, are biologically active. For example, certain hydrocarbon members of the carotenoid family (most notably, β-carotene, or pro-vitamin A, one of the most abundant carotenoids in food) are sources of retinol (one form of vitamin A). Carotenoids protect plants from photosensitized oxidative damage, probably by deactivating singlet oxygen. Epidemiological evidence indicates that carotenoid intake correlates inversely with the incidence of some types of cancer (Peto et al, Nature, 1981, 290, 201–208). Carotenoids and retinoids have been shown to retard the development of some experimentally induced animal tumors (N. I. Krinsky, Actions of Carotenoids in Biological Systems, *Annu. Rev. Nutr*, 13, 561–587 (1993); Matthews-Roth, *Curr. Top. Nutr. Dis.* (*New Prot. Roles Select. Nutr.*), 1989, 22, 17–38; *Pure Appl. Chem.*, 1985, 57, 717–722). A number of dietary intervention studies are being carried out to try to determine the efficacy of supplemental β-carotene as a non-toxic, dietary anticarcinogen that can effectively decrease cancer mortality. Recently, the possibility has begun to be examined that β-carotene may be associated with decreased incidence of coronary heart disease. Recent clinical data using related compounds (retinoids—retinoic acid, retinol, and retinamides) have demonstrated a role in anti-cancer therapy, both as a therapeutic and a preventive agent (cancers of the skin, head and neck, lung and bladder, acute promyelocytic leukemia, leukoplakia and myelodysplastic syndromes; D. L. Hill and C. J. Grubs, Retinoids and Cancer Prevention, *Annu. Rev. Nutr.* 1992, 12, 161–181). Furthermore, β-carotene has antioxidant properties at the low oxygen pressures found in tissues (Burton and Ingold, β-Carotene: an unusual type of lipid antioxidant, *Science*, 1984, 224, 569–573).

The protective effect of lactation and dietary carotenoids in breast cancer development has been reported (American Cancer Society, 1996; Holmes, Hunter, & Willett, 1995, Stoll, 1996; and Weisburger, 1991). However, little is known about the role of lactation in influencing transport of carotenoids into the micro environment of the breast.

SUMMARY OF THE INVENTION

In one embodiment, the invention provides a method for detecting a biological factor in a fluid sample obtained from a mammary gland, comprising non-invasively obtaining a mammary gland fluid from a subject by warming the mammary gland; massaging the mammary gland from the chest wall towards the nipple; extracting the mammary fluid from the nipple by expression and/or aspiration and detecting the biological factor in the mammary gland fluid.

In another embodiment, the invention provides a method of determining a risk of a mammary gland disease in a subject comprising non-invasively obtaining a mammary gland fluid from the subject, comprising warming the mammary gland; massaging the mammary gland from the chest wall towards the areola or nipple; and aspirating the mammary fluid; quantifying the amount of a biological factor in the mammary fluid; comparing an amount of the biological factor to the amount of the biological factor in a control sample, wherein the ratio of the biological factor in the fluid to the control sample is indicative of the risk of mammary gland disease.

In yet another embodiment, the invention provides a method of determining the risk of breast cancer in a subject comprising quantifying the amount of a carotenoid in a biological sample obtained from a mammary gland compared to an amount of a carotenoid in a control sample, wherein if a ratio of carotenoids in the biological sample to the carotenoids in the control sample is less than one the ratio is indicative of a risk of breast cancer.

In another embodiment, the present invention provides a method for increasing the amount of carotenoids in a mammary gland, comprising warming the mammary gland; massaging the mammary gland from the chest wall towards the areola or nipple; and aspirating a mammary fluid from the mammary gland.

In another embodiment, the invention provides a non-invasive method for obtaining a biological sample from a mammary organ of a subject, comprising massaging the mammary gland tissue from the chest wall towards the nipple; placing the thumb and first fingers behind the nipple forming a C-hold; pushing the nipple into the chest wall; and rolling thumb and fingers forward toward the nipple.

In yet another embodiment, the invention provides an apparatus for collection of a biological sample from the mammary gland of a subject, comprising a nipple receiving unit having a tubular shape with a nipple receiving end designed to receive a nipple and a second vacuum attachment end for attachment to a vacuum line; a vacuum line having a first and a second end, wherein the second end is attached to the vacuum source and the first end is attached to the nipple receiving unit; and a vacuum source wherein the vacuum source is in vacuum communication with the nipple receiving end of the nipple receiving unit.

In another embodiment, the invention provides an apparatus for collection of a biological sample from a mammary gland of a subject, comprising a pliable mammary gland shield configured to fit snugly over the mammary gland of the subject, the shield having a massaging element configured to provide physical stimuli to the mammary gland; a nipple receiving unit centered radially in the mammary gland shield, wherein the nipple receiving unit comprises a tubular shape with a nipple receiving end designed to receive a nipple and a second vacuum attachment end for attachment to a vacuum line; a vacuum line, the vacuum line having a first end and a second end, the first end being connected to the nipple receiving unit; a vacuum source for creating a vacuum connected to the second end of the vacuum line, wherein the vacuum source is in vacuum communication with the nipple receiving end of the nipple receiving unit.

BRIEF DESCRIPTION OF THE DRAWINGS

FIG. 2A shows a massaging technique for massaging the mammary gland.

FIG. 2B shows a "C-Hold" technique used to express mammary fluids from the human breast.

FIG. 3 is a diagram of a nipple aspirator unit.

DETAILED DESCRIPTION OF THE INVENTION

Figure 1:
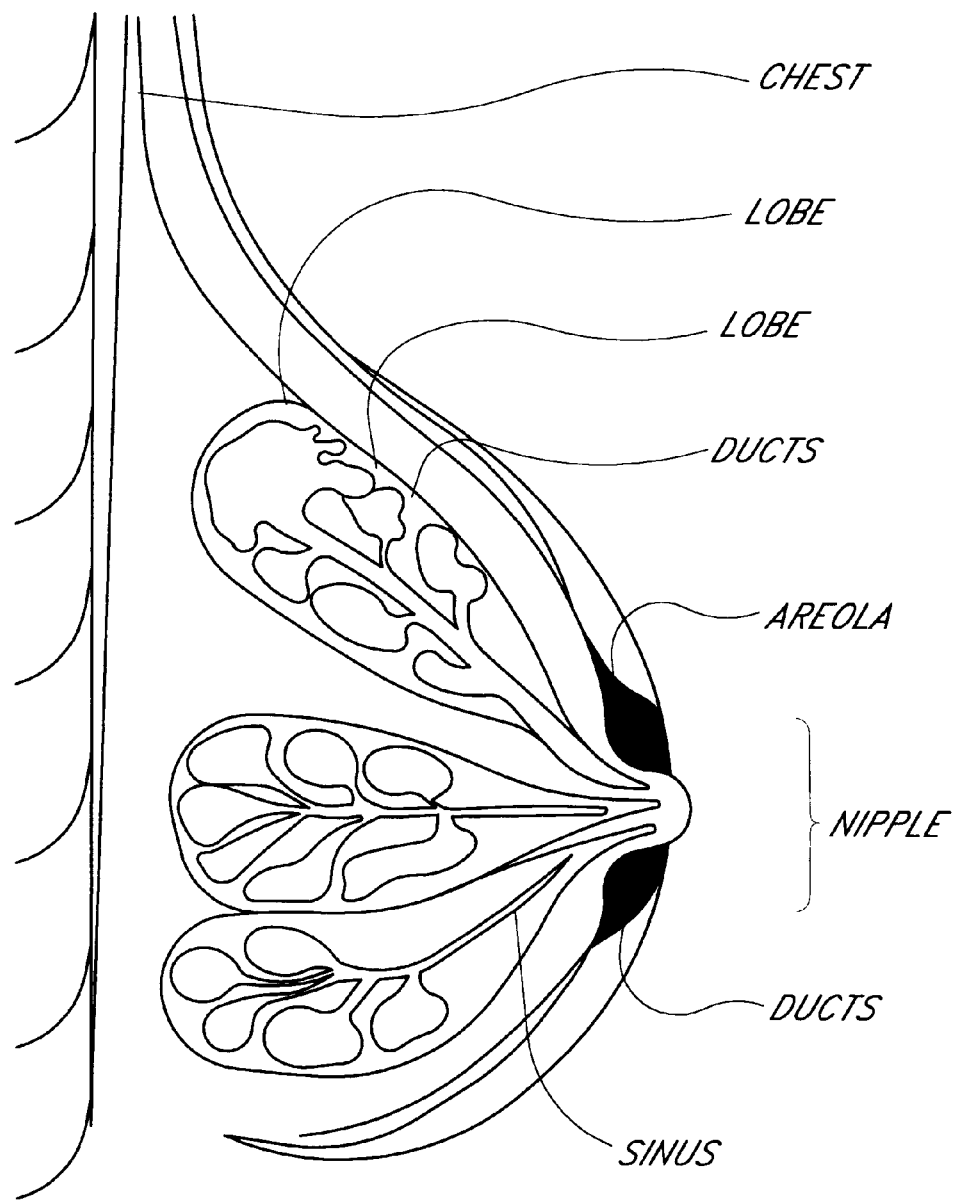
FIG. 1 shows the anatomy of the human mammary gland.

The present invention discloses a method and apparatus useful in determining and affecting the risk of breast cancer in mammals. During the physiological process of lactation, the fluid micro environment of the mammary gland is in a process of fluid synthesis and drainage. Changes in the mammary gland epithelium lining the ducts of the mammary gland during differentiation and growth, in the preparation for milk production, is thought to alter the susceptabilty of the cells of the mammary gland to neoplastic changes. During lactation, the cells of the mammary gland undergo a flushing process, whereby renewal of fluids in the mammary gland flushes potential carcinogens in the ducts as well as brings new fluids in contact with the cells. In the absence of such a flushing process, waste materials, including biochemical waste products and carcinogenic agents, accumulate and concentrate in the cellular tissue of the mammary gland. In addition, stasis in the fluid environment of the mammary gland, which can specifically occur during lactation failure or upon termination of breast feeding, causes the cellular environment of the mammary gland tissue to become alkaline. Such alkalinity has been demonstrated to result in increased mitotic activity and cell proliferation.

As used herein, a "biological factor" is meant to include any number of biological active cells, proteins, chemicals (e.g., carotenoids), lipids, growth factors, cytokines, nucleic acid molecules (i.e., DNA or RNA). For example, mammary gland fluid may contain whole mammary fluid, whole cells, cell fragments, cell membranes, various liquids, cellular or other solid fractions of the mammary fluid, proteins, glycoproteins, peptides, nucleic acids, lipids and other biochemical factors. For example, and not by way of limitation, proteins including HER2 (neu), a growth factor receptor found within tumor cells indicative of an aggressively growing tumor, Ki67, cyclin D1 and PCNA; antigens such as, for example, carcinoembryonic antigen (CEA) and prostate specific antigen (PSA); lipid molecules including, for example, cholesterol, hormones, cholesterol oxides; growth factors including, for example, members of the TGFβ superfamily, TNF, and EGF are all capable of detection using the apparatus, kits, and methods of the invention. Tumor growth can be evaluated using a number of growth factor and hormone markers (e.g., estrogen, EGF, erbB-2, and TGF-α), receptors of autocrine or exocrine growth factors and hormone (e.g., IGF and EGF receptors) as well as angiogenic factors such as VEGF, PDGF and others.

As used herein, a "biological sample" is meant to include tissue, serum, plasma, mammary gland fluid, milk, nipple aspirate and colostrum. The biological sample comprises a biological factor. Accordingly, a control or standard sample may be a biological sample or a synthetic sample having a known amount of a biological factor.

As used herein, a "breast disease indicator" means any protein, peptide, glycoprotein, lipid, glycolipid, proteolipid, nucleic acid or other biochemical or molecular factor that is uniquely indicative of a mammary gland tissue disease, such a cell proliferative disorder or neoplasia. Such a breast disease indicator is measurably increased or decreased in the mammary gland tissue, such as the epithelial cells of the ducts of the mammary gland, compared to a normal standard sample.

A representative subset of breast disease indicators include breast cancer markers. Such breast cancer markers that are useful within the methods of the invention are described in Porter-Jordan et al., *Hematol. Oncol. Clin. North Amer.* 8:73–100, 1994; and Greiner, *Pharmaceutial Tech.*, May, 1993, pp. 28–44, each of which is incorporated herein by reference. Also included within the scope of the invention is a non-invasive method for the detection of mammaglobin, a mammary-specific secretory protein, and mammaglobin nucleic acids as disclosed in U.S. Pat. No. 5,855,889, the disclosure of which is incorporated herein by reference.

In one embodiment, the invention provides a method for the detection of a biological factor present in the mammary gland of a subject. In a this embodiment, the biological factor is detected in a mammary fluid obtained from the mammary gland. In another embodiment, the invention provides a method and apparatus for the detection of a mammary gland disease by detecting the presence or absence of a biological factor in a mammary gland fluid. The method and apparatus provide for a non-invasive technique for measuring a biological factor representing a breast disease indicator. The presence or absence of a breast disease indicator is indicative of the presence of a mammary gland disease.

The inventors have found that during lactation, the level of carotenoids in mammary gland tissue is about the same level as found in the serum of a subject. Furthermore, the concentration of carotenoids is inversely proportional to the amount of time post-lactation or post-fluid expression. In other words, the amount of carotenoids in the mammary gland tissue decreases following termination of lactation or milk-expression. As carotenoid levels decrease, the number of oxidative scavengers also decreases, resulting in an increase in the susceptibility of the tissue to oxidative damage and potentially neoplastic growth. The inventors believe that by stimulating fluid secretion from the mammary gland, in the absence of oxytocin administration, carotenoid levels are replenished and increased in a mammary gland fluid. In some embodiments, oxytocin may be administered to increase fluid secretion. The oxytocin can be exogenous oxytocin such as oxytocin present in a pharmaceutical composition that may be administered nasally or by buccal administration (Dawood, Ylikorkala, & Fuchs, American Journal of Obstetrics and Gynecology, 138, 20–24. 1980). Oxytocin has a specific influence on the myoepithelium cells of the distal ducts (Gaitan et al., Endocrinology, September 1967; 81(3):515–20) Accordingly, such exogenous oxytocin will help fluid collection. Alternatively, transcutaneous electrical stimulation may be used to induce endogenous oxytocin by stimulation of the cutaneous branches of the 4th intercostal nerve (Sarhadi et al., 1996; Sarhadi, Shaw-Dunn, & Soutar, Br J Plast Surg December 1997, 50(8):668–70) and the nipple using TENS (Seoud et al., J Reprod Med, June 1993;38(6): 438-42).

In epidemiological studies designed to investigate the protective effect of lactation and breast cancer risk, the independent protective effect of lactation was supported for premenopausal, but not postmenopausal women. Mammary involution at menopause represents a significant epithelial regression and loss followed by replacement of ductal and lobular structures by adipose tissue (Forbes, 1986). These anatomical changes result in a decreased blood flow and nutrient delivery. Using the methods and apparatus of the present invention, it is possible to increase the amount of carotenoids in the mammary gland and/or mammary fluids of non-lactating subjects by stimulating and/or aspirating fluid expressed from the nipples of the subject, thus simulating the flushing process of a lactating or breast feeding subject. As mentioned above, decrease in carotenoids in the mammary gland tissue deceases the number of oxidative scavengers in the mammary gland tissue. This decrease may increase the risk of oxidative damage to the mammary gland tissue and thus increase the chance of cell proliferative disorders, neoplasia, and cancer. To overcome the decrease in carotenoids levels and increase the level of such oxidative scavengers, the invention provides a method and apparatus for stimulating fluid "turnover" in the mammary tissue by stimulating and/or aspirating fluid from the mammary gland of a non-lactating subject. Without being limited to any particular theory, it is the result of the fluid turnover in the mammary tissue that brings carotenoids from other tissues and/or the blood stream of the subject into the mammary tissue. The invention provides a non-invasive method for stimulating fluid turnover in the mammary gland of a subject in order to increase blood flow and nutrient delivery.

In another aspect, the invention provides a method for determining the risk of breast cancer in a subject by detecting the amount of carotenoids in mammary gland fluid of a subject. The subject may be any mammal, but is preferably a human. A biological sample obtained by stimulated secretion from the mammary gland of the subject is measured to determine the level of a biological factor (e.g., a carotenoid level). The level of the biological factor in the sample is measured against a standard sample. In one embodiment, the standard sample is the level of the biological factor (e.g., carotenoid level) in the serum of the same subject.

In particular, during or after aspiration of the mammary fluid, a fluid sample is collected from the nipple of the mammary gland. The mammary fluid can be collected in any number of ways including, but not limited to, directly aspirating the mammary fluid into a collection device and/or rinsing the nipple with a buffer and collecting the rinse into a suitable collection device.

Detection and/or quantification of a biological sample of the invention can be performed in any number of ways depending upon the type of biological factor being measured. Generally, a biological sample collected according to the methods of the invention is exposed to a probe that specifically interacts with a biological factor to be measured (e.g. a breast disease indicator). For example, where the biological factor or breast disease indicator is a peptide, polypeptide or protein the methods may utilize well known ELISA immunoassay, immunoprecipitation assays, Western blots, dot blots and affinity purification assays to name but a few. Where the biological factor is a nucleic acid, techniques including, for example, hybridization assays at standard or high stringency to detect DNA or RNA using suitable non-antibody probes can be used (e.g., Northern blots, Southern blots, dot blots). Alternatively, PCR may be use to amplify and then detect DNA or RNA using techniques common in the art. Where the biological factor to be measured is a lipid or biochemical compound, the biological sample can be extracted using extraction techniques, such as lipid extraction techniques, and the biological factor detected or quantified by liquid chromatography, such as High-Performance-Liquid-Chromatography (HPLC). Such chromatography techniques are well known in the art and are particularly suited for the detection of carotenoids, cholesterol, cholesterol byproducts, flavorins, prostaglandins, leukotrienes and hormones. Whole cells or cellular debris present in the biological sample (e.g., the mammary fluid) may also be analyzed to determine the presence or absence of a disease or disorder. Standard cell culture techniques may be used to culture, maintain or expand a population of cells present in the sample. Cells present in the sample may be analyzed by histological techniques, stains, or standard microscopy techniques that can detect, for example, morphological characteristics of cells obtained from the fluid sample.

The invention further provides methods wherein the biological samples, such as mammary gland fluids, are obtained non-invasively. By non-invasive is meant that non-surgical or non-invasive techniques are used, such that the tissue of the mammary gland or mammary tissue is not penetrated by needles or other devices.

To non-invasively obtain the biological sample from the mammary gland and/or increase fluid turnover in the mammary gland, the inventors have developed a method whereby a lactating subject and/or a non-lactating subject can obtain mammary gland fluids from the mammary gland. The method can be done manually or by utilizing an apparatus of the invention, as described more fully below. In one embodiment, the carotenoid levels in mammary gland fluid are increased using the following procedures:

Cleansing: The mammary gland and/or nipple area are preferably cleansed in a manner designed to remove keratin plugs that may be blocking duct openings. For example, the mammary gland and/or nipple may be cleansed with a detergent, or baking soda and water.

Warming: The mammary gland is warmed sufficiently to increase fluid flow from the gland. Warming of the mammary gland can be done in any number of ways including, but not limited to, warming with a heating blanket, heating bag, warmed wash cloth or compresses, heating bottle, and other methods known in the art. Without being limited to any particular theory, such warming may result in the opening of pores and ducts in the mammary gland as well as dilation of capillaries in the mammary tissue, thus increasing fluid flow from the mammary gland.

Massaging: The mammary gland is massaged to promote or cause fluid expression. Massaging of the mammary gland can be performed in any number of ways so long as there is a physical stimulation to the tissue of the breast. The stimulation maybe provided by a device or apparatus designed to deliver a stimulatory action, or an appendage, hand or digit of the subject. For example, the tissue may be massaged by using a vibration device such as the apparatus below or by other vibration devices easily identifiable by those skilled in the art, by physical manipulation using a device or by physical manipulation using a hand. In a one embodiment, the tissue of the breast is massaged from the chest wall towards the nipple of the mammary gland. The method as includes gently massaging the breast tissue around the chest wall with one hand while supporting the breast with the other hand. Massaging is generally in the direction from the chest wall towards the areola and nipple. This technique uses a slight shaking or vibrating movement with the fingers, while at the same time moving around the breast gradually until the entire breast is massaged (FIG. 2A).

Expression/Aspiration: Fluid from the mammary gland is extracted by expression and/or aspirations. Expression or aspiration of mammary fluid can also be performed in any number of ways. For example, a suction device which engages the mammary gland, preferably the nipple, may be used to create a suction to assist in aspirating mammary fluid from the ducts of the mammary gland. In one embodiment, a nipple receiving unit attached to a vacuum line (e.g., a tube or hose) is used to aspirate mammary fluid. In a one embodiment, the nipple receiving unit is attached to a first end of the vacuum line and a syringe is attached to a second end of the vacuum line, wherein withdrawal of the plunger of the syringe delivers a partial vacuum to the nipple receiving unit. The nipple receiving unit may be of a coaxial design having an internal cylindrical shape for receiving the nipple at a first end and providing a vacuum at the second end. The outer cylindrical shape providing support.

The vacuum line can be made of any material which does not collapse under vacuum force, for example, latex tubing. The nipple receiving unit can be made out of any material sufficiently rigid to provide for resilience under vacuum. Preferably, the material can withstand repeated cleanings using detergents, heat, and or sterile gas, (for example, plexiglass or polymer materials).

To aspirate mammary fluid using the nipple aspirator unit, the inner cylinder of the nipple receiving unit is centered over the nipple of the subject, and held in place. A partial vacuum is then applied to the nipple receiving unit for about 30 seconds and released. A negative (i.e., vacuum) pressure of about −150 mm/Hg to about −300 mm/Hg, typically about −240 mm/Hg is applied to the nipple. In one embodiment, the plunger of a syringe attached to a vacuum line which is in-turn attached to a nipple receiving unit is withdrawn sufficiently to create a partial vacuum (e.g., about 10 cc of pull) for about 30 seconds.

Alternatively, expression or aspiration of mammary fluid can be performed by manipulation of the mammary gland and the nipple by holding the breast in a "C-hold" by positioning the thumb and first fingers about 1 to 1.5 inches behind the nipple, with the thumb above the nipple and the fingers below. The breast is then pushed into the chest wall and the thumb and fingers rolled forward towards the nipple (see FIG. 2B). If this method is performed, squeezing the mammary gland should be avoided to prevent bruising of the mammary tissue. Either of these techniques are continued for a sufficient amount of time until visualization of mammary fluid.

Once nipple aspirate or mammary fluid appears, the fluid can be collected in any number of ways including, but not limited to, directly aspirating the mammary fluid into a collection device and/or rinsing the nipple with a buffer and collecting the rinse into a suitable collection device. Suitable collection devices include, for example, a microscope slide, a filter, matrix, or vessel.

The present invention further provides an apparatus useful in obtaining mammary fluids. Reference to FIG. 3, is a diagram of a nipple aspirator unit 10 having a vacuum line 30 with a first end 31 and a second end 32, wherein first end 31 is attached to and in vacuum communication with a nipple receiving unit 20. The vacuum line 30 is attached at its second end 32 to a vacuum source 40.

Figure 4A:
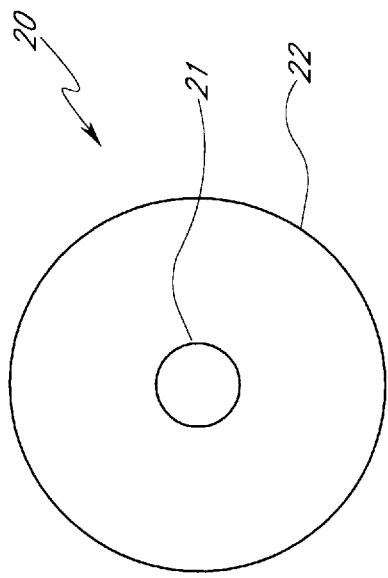
FIG. 4 is a diagram showing the nipple receiving unit 20 in further detail.
Figure 4B:
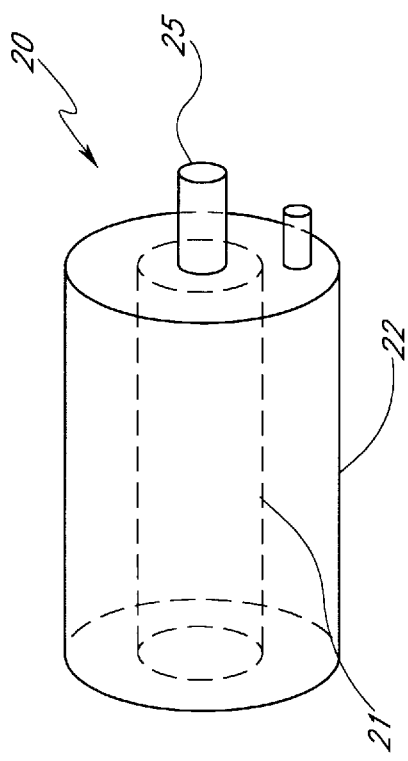

FIG. 4 shows the nipple receiving unit 20 in further detail. The nipple receiving unit 20 is substantially tubular and of a solid material having at its first end a connector 25 for connecting to a vacuum source and a second end 26 designed to fit and receive a nipple making an air tight seal. The nipple receiving unit may be further attached to a breast shield 27. The breast sheild 27 can additionally have numerous features, for example and not by way of limitation, a massaging element, a vibrating element or any number of features designed to deliver a physical stimulus to the mammary gland.

In addition to the methods and apparatus described above, the invention further provides kits comprising reagents and components for practicing the methods and assay techniques of the invention. Such a kit may also include a carrier means being compartmentalized to receive in close confinement one or more containers such as vials, tubes, and the like, each of the containers comprising one of the separate elements to be used in the method. For example, the kits may contain components for obtaining a biological sample, which components include a nipple aspirator unit, a vacuum line; and a collecting device for collecting the biological sample, which collection device may range from a simple fluid reservoir to solid phase media for use in a solid phase assay system.

In more detailed embodiments, the kits include reagents and/or devices for detecting the presence of a biological factor in a biological sample obtained non-invasively from a mammary gland. The kits may include, for example, buffers, preservatives, and probes. Such probes may include a monoclonal antibody, polyclonal antibody, a nucleic acid, or enzyme. Such probes can be attached to a solid substrate.

The above disclosure generally describes the present invention. A more complete understanding can be obtained by reference to the following specific examples which are provided herein for purposes of illustration only and are not intended to limit the scope of the invention.

EXAMPLES

Women between the ages of 18 and 45 yeas of age and non-pregnant were recruited for participation the study. Criteria for inclusion for the breast-feeding group included delivery of full term infant 2 months prior and that the child was as lest six months and totally weaned from breast feeding for at least three months. After cessation of lactation, mammary involution occurs over a three-month period, resulting in a return to a non-secretory alveolar lining. Women participating in this study were minimally three-months post-wean to control of the physiologic changes that occur during lactation and subsequent to cessation of lactation. Criteria for inclusion for the non-breast-feeding group included delivery of a full-term infant 24 months prior and selecting of formula feeding the infant. Exclusion criteria or withdrawal from the study included pregnancy.

Recruitment of subjects occurred in three-Midwest metropolitan cities through subject referral, study recruitment fliers at women' health clinics, WIC offices, daycare centers, and public health clinics, and advertisements in the newspaper. Over 100 women were recruited to participate in the study, however, only 85 women met the inclusion criteria of the study. Of these, 43 women were able to express breast fluids sufficiently and had plasma carotenoid available for analysis.

A nipple aspiration device was designed to assist in the aspiration of breast fluid. A kit containing microtubes and the aspiration device necessary for collection of breast fluid was developed. A breast fluid sample collection protocol using a nipple aspiration method to obtain breast fluids over a period of 17 days was used. Generally, the method included washing the nipple area with a detergent, such as baking soda and water to remove keratin plugs. The breast is then warmed to increase fluid and blood flow to the breast by warming the breast with a warm towel or taking a warm shower. The breast is then massaged around the chest wall with one hand while supporting the breast with the other hand, massaging from the chest wall towards the areola and nipple area using a slight shaking movement with the fingers, this is performed until the entire breast is massaged. Fluid was expressed by positioning the thumb and first two fingers about 1 to 1.5 inches behind the nipple, pushing straight into the chest wall, rolling the thumb and fingers forward and repeating the method until sufficient fluid was expressed. A typical protocol is as follows:

Starting one week prior to the scheduled visit, the subject will prepare breasts daily as follows: 1) Use a towel following shower/bath to gently cleanse the nipples, removing traces of dry skin daily; 2) Apply a solution of ⅛ teaspoon of baking soda½ cup of water to the nipple for 10–20 minutes covering each with a breast pad and securing in place with a bra. After 10–20 minutes, the solution is washed off and any dry skin is removed. The subject will then use of a small amount of HEB creme (hydro-emollient base pharmaceutical creme) to the nipple. The subject then expresses fluid from the nipple by using the C-hold technique, a nipple aspiration device or a combination of both.

This is typically performed in the absence of oxytocin, however, where there appears to be difficulty in expressing fluids, exogenous oxytocin may be administered. Alternatively, endogenous oxytocin stimulation may be achieved by electrical stimulation as described above. Any fluid the is expressed is collect in microtubes. All collection tubes will be labeled to coincide with the step and breast used for aspiration. A 10 μl sample from each breast will be placed in a cytology micro-tube with Preserv-Cyt, refrigerated for cytology studies. The remaining fluids and serum are placed in amber micro-tubes. The serum is centrifuged, divided, and prepared for distribution, stored at −70 C. and delivered within 48 hours for carotenoid and tocopherol assays.

Some women were provided nipple aspiration device for obtaining mammary fluid. These women were instructed to place the nipple aspirator portion of the nipple aspirator centered over the nipple and pulling the plunger of the syringe to the 10 cc mark and holding to a count of 30. If difficulty was found in aspirating fluid, the women were instructed to use a larger syringe and/or pull back the plunger an additional 10 cc (i.e., 20 cc) for a count of 30. As fluid appeared at the nipple, the fluid was collected into a capillary tube and aliquoted into microtainers. Fluid was stored in amber opaque microtainers to shield against light which degrades carotenoids. Blood sampling equipment, including alcohol, butterfly needles, and collection tubes containing EDTA and sodium heparin were used to collect blood for carotenoid assay. Plasma was stored in amber opaque microtainers.

Plasma and breast fluid samples were collected in amber microtubes until assay. Blood was centrifuged immediately after collection and the plasma withdrawn and stored in amber capillary tubes. Carotenoid levels in both plasma and breast fluids were determined by spectrophotometric techniques as described by Patton et al. (1980).

Mammary fluid was collected every other day for 17 days. If a participant was unable to collect fluid using the aspirator within 30 minutes of the attempt, the subject was instructed to stop and try again in two days. The first eight collections of breast fluid were pooled into an microtube, protected from the light, and maintained in the freezer between collections. An initial blood sample was collected into a tube containing EDTA.

Eighty-one samples were analyzed for carotenoid level. The mean plasma carotenoid level was 1.83 mcg/ml (SD= 0.89, range 0.037–4.50 mcg/ml). The mean plasma carotenoid level reported in this study is consistent with levels reported in epidemiologic studies measuring plasma carotenoid (Potischman, 1990). The total number of women with both plasma and mammary fluid carotenoid levels numbered 43. The overall mean breast fluid carotenoid level was 1.73 mcg/ml (SD −1.7, range 0–10.20 mcg/ml). This finding was consistent with the mean breast fluid carotenoid level (1.94 mcg/ml) reported by Covington et al. (1998) for women post weaned.

Age significantly influenced the relation between plasma and breast fluid carotenoid levels, as illustrated in Table 1. A significant negative partial regression coefficient for plasma and age indicated a significant negative interaction. Thus the relation between plasma and mammary fluid carotenoid levels diminished with age. The results of the hierarchical regression did not support the influence of parity (See Table 2). The influence of length of time post-wean on the relation between plasma and breast fluid carotenoids levels was supported (See Table 3). Thus the relation between plasma and breast fluid carotenoid levels diminished with the increasing duration of time since cessation of lactation.

TABLE 1

Hierarchical Regression For Breast Fluid Carotenoid on Plasma Carotenoid and Age

| Variable | β | ΔR² | p |
|---|---|---|---|
| Step 1 Plasma Carotenoid | −.37 | .13* | .02 |
| Step 2 Age | .21 | .04 | .17 |
| Step 3 Plasma Carotenoid × Age | −.33 | .10 | .03† |

Note
*R²; †partial = −.35

TABLE 2

Hierarchical Regression For Breast Fluid Carotenoid on Plasma Carotenoid and Parity

| Variable | β | ΔR² | p |
|---|---|---|---|
| Step 1 | −.37 | .13* | .02 |
| Parity | | | |
| Step 3 | −.11 | .01 | .47 |
| Plasma Carotenoid × Parity | | | |

Note
*R²

TABLE 3

Hierarchical Regression For Breast Fluid Carotenoid on Plasma Carotenoid and Length of Time Post-Wean

| Variable | β | ΔR² | p |
|---|---|---|---|
| Step 1 | −.39 | .16* | .03 |
| Plasma Carotenoid | | | |
| Step 2 | .18 | .03 | .36 |
| Months Post-Wean | | | |
| Step 3 | −.48 | .21 | .007† |
| Plasmid Carotenoid × Months Post-Wean | | | |

Note
*R²: †partial = −.51

Hierarchical regression analysis with a one-tailed test of significance was used to examiner the influence of lactation on the relation between plasma and breast fluid carotenoid levels. As illustrated in Table 4, the significant beta value in Step 3 of the hierarchical regression analysis in addition to the significant change in the R2 when the recent lactation entered the hierarchical regression equation with plasma carotenoid, signified the presence of an influence of recent lactation on the relation between plasma and breast fluid carotenoid levels. A significant positive partial regression coefficient for plasma carotenoid×lactation indicated a significant positive interaction. Thus, the influence of lactation on the relation between plasma and mammary fluid carotenoid levels was supported. Additionally, the longer a woman breast fed her last child, the greater the positive relation between plasma and breast fluid carotenoid levels. (See Table 5).

TABLE 4

Hierarchical Regression For Breast Fluid Carotenoid on Plasma Carotenoid and Lactation

| Variable | β | ΔR² | p |
|---|---|---|---|
| Step 1 | −*37 | .14* | .008 |
| Plasma Carotenoid | | | |
| Step 2 | −.16 | .03 | .14 |
| Lactation | | | |
| Step 3 | .20 | .04 | .09† |
| Plasma Carotenoid × Lactation | | | |

Note
*R²; †partial = .21

TABLE 5

Hierarchical Regression For Breast Fluid Carotenoid on Plasma Carotenoid and Cumulative Lifetime Duration of Lactation

| Variable | β | ΔR² | p |
|---|---|---|---|
| Step 1 | −.36 | .13* | .01 |
| Plasma Carotenoid | | | |
| Step 2 | .07 | .004 | .34 |
| Plasma Carotenoid × Cumulative Duration of Lactation | | | |

Note.
*R² × Parity
Note.
*R²; †p = .04, partial = −.47

TABLE 6

Hierarchical Regression For Breast Fluid Carotenoid on Plasma Carotenoid and Lactation Age, Parity, and Length of Time Post-Wean Serving Together as Moderators

| Variable | β | ΔR² | p |
|---|---|---|---|
| Step 1 | −.38 | .15* | .04 |
| Plasma Carotenoid | | | |
| Step 2 | | .07 | .78 |
| Age | .18 | | |
| Lactation | −.03 | | |
| Months Post-Wean | .15 | | |
| Parity | .002 | | |
| Step 3 | | .31 | .05 |
| Plasma Carotenoid × Months Post-Wean | −.59† | | |
| Plasma Carotenoid × Age | −.40 | | |
| Plasma Carotenoid × Lactation | −.16 | | |
| Plasma Carotenoid | .31 | | |

A significant negative partial regression coefficient for plasma carotenoid and length of time post-wean indicated a significant negative interaction. Thus, in the model, length of time post-wean diminished the relation between plasma and breast fluid carotenoid levels and altered the influence of recent lactation and age on the relation between plasma d breast fluid carotenoid levels.

A negative partial regression coefficient for length of time post-wean influenced the relation between plasma and breast fluid carotenoid levels (See Table 7). A negative partial regression coefficient for length of time-post wean indicated a significant negative influence. This, the influence of cumulative lifetime duration of lactation and parity was not altered, but age did not diminish the relation between plasma and breast fluid carotenoid levels as reported in separate analysis, while length of time post-wean did significantly diminish the relation between plasma and breast fluid carotenoid levels.

TABLE 7

Hierarchical Regression For Breast Fluid Carotenoid on Plasma Carotenoid and Cumulative Lifetime Duration of Lactation Age, Parity, and Length of Time Post-Wean Serving Together as Moderators

| Variable | β | ΔR² | p |
|---|---|---|---|
| Step 1 | −.38 | .15* | .04 |
| Plasma Carotenoid | | | |
| Step 2 | | .07 | .77 |

TABLE 7-continued

Hierarchical Regression For Breast Fluid Carotenoid on Plasma Carotenoid and Cumulative Lifetime Duration of Lactation Age, Parity, and Length of Time Post-Wean Serving Together as Moderators

| Variable | β | ΔR² | p |
|---|---|---|---|
| Age | .17 | | |
| Cumulative Duration of Lactation | −.08 | | |
| Months Post Wean | | | |
| Parity | .06 | | |
| Step 3 | | .32 | .04 |
| →Plasma Carotenoid × Months Post-Wean | −.62† | | |
| →Plasma Carotenoid × Age | −.40 | | |
| →Plasma Carotenoid × Cumulative Duration of Lactation | −.20 | | |
| →Plasma Carotenoid × Parity | .37 | | |

Note.
*$R^2$; †p = .05, partial = −.45

The results indicate that age influenced the relation between plasma and breast fluid carotenoid levels, the relation between plasma and breast fluid carotenoid levels diminishing as age increased. This was true for all women, regardless of lactation status. The American Cancer Society (1996) reports that the incidence of breast cancer increases with age and breast cancer mortality rates increase for women 40–54 years of age.

Parity did not significantly influence the relation between plasma dnd breast fluid carotenoid levels. Furthermore, greater length of time post-wean significantly reduced the relation between plasma and breast fluid carotenoid levels. The results indicate that the relation between plasma and breast fluid carotenoid levels diminished the longer the time post-wean. Since the longer the time post-wean indicates a longer period of time away from the positive influence of lactation as a potentiating process. Additionally, post-lactation, the breast undergoes mammary involution over a three-month period of time, in which the number of mammary alveoli are reduced and blood flow and nutrient delivery is diminished (Lawrence, 1994, Neville & Niefert, 1983).

Lactation had a significant positive influence on the relation between plasma and breast fluid carotenoid levels. The results of previous epidemiologic studies on lactation and breast cancer risk supports a protective effect, however, the mechanism is unknown. Lactation, a physiologic process in which blood flow and nutrient transport to the breast increase the delivery of available circulating plasma carotenoids into the micro-environment of the breast in women who breast-feed, especially at shorter periods post-wean. Lactation positively influenced the relation between plasma and breast fluid carotenoid levels. This positive influence was detected at 15–35 months postpartum.

The foregoing description and examples of the invention are exemplary for purposes of illustration and explanation. It should be understood that various modifications can be made without departing from the spirit and scope of the invention. Accordingly, the following claims are intended to be interpreted to embrace all such modifications.

What is claimed is:

1. A method of determining a risk of a mammary gland disease in a subject comprising:
   non-invasively obtaining a mammary gland fluid from the subject, comprising
   warming the mammary gland;
   massaging the mammary gland;
   aspirating the mammary fluid;
   quantifing the amount of a biological factor in the mammary fluid; and
   comparing an amount of the biological factor to the amount of a biological factor in a control sample, wherein the ratio of the biological factor in the fluid to the control sample is indicative of the risk of mammary gland disease.

2. The method of claim 1, further comprising:
   placing the thumb and first fingers behind the nipple forming a C-hold;
   pushing the nipple into the chest wall; and
   rolling thumb and fingers forward toward the nipple.

3. The method of claim 1 or 2, further comprising applying a nipple aspirator unit to the nipple, the nipple aspirator comprising:
   a nipple receiving unit having a nipple receiving end and a vacuum attachment end;
   a vacuum source;
   a vacuum line having a first and second end wherein the first end is connected to the nipple receiving unit at the vacuum attachment end and the second end is connected to the vacuum source such that the vacuum source is in vacuum communication with the nipple receiving end of the nipple receiving unit.

4. The method of claim 1, wherein the biological factor is selected from the group consisting of a nucleic acid, a protein, a peptide, a glycoprotein, a lipid and a biochemical product.

5. The method of claim 4, wherein the nucleic acid is DNA or RNA.

6. The method of claim 4, wherein the biochemical product is β-carotene or a derivative thereof.

7. The method of claim 6, wherein the biochemical product is detected by chromatography.

8. The method of claim 1, wherein the biological factor is quantified by employing a probe that specifically interacts the biological factor.

9. The method of claim 7, wherein the probe is selected from the group consisting of a monoclonal antibody, a polyclonal antibody, and a nucleic acid.

10. The method of claim 6, wherein the biochemical product is a carotenoid.

11. The method of claim 1 or 2, wherein the step of massaging the mammary gland comprises massaging the mammary gland from the chest wall towards the areola or nipple.

12. The method of claim 1, wherein the subject is a mammal.

13. The method of claim 12, wherein the mammal is a human.

14. The method of claim 1, wherein the method further comprises warming the mammary gland prior to massaging.

15. The method of claim 1, wherein the subject is administered oxytocin prior to massaging the mammary gland.

16. The method of claim 3, wherein the nipple receiving unit has a tubular shape with a nipple receiving end designed to receive a nipple.

17. The method of claim 3, wherein the vacuum source is a syringe.

18. The method of claim 3, wherein the vacuum source is a vacuum pump.

19. The method of claim 3, wherein the vacuum source is a wall vacuum.

20. The method of claim 3, wherein the nipple receiving unit comprises an inner tube and an outer tube, wherein the inner tube and the outer tube are coaxial.

21. The method of claim 3, the nipple aspirator unit further comprising a breast shield having the nipple receiving unit concentrically positioned in the breast shield.

22. The method of claim 21, wherein the breast shield further comprises a vibrating element.

23. The method of claim 21 or 22, wherein the breast shield further comprises a massaging unit.

24. The method of claim 1 or 2, further comprising applying a nipple aspirator unit to the nipple, the nipple aspirator comprising:

a pliable mammary gland shield configured to fit snugly over the mammary gland of the subject, the shield having a massaging element configured to provide physical stimuli to the mammary gland;

a nipple receiving unit centered radially in the mammary gland shield, wherein the nipple receiving unit comprises a tubular shape with a nipple receiving end designed to receive a nipple and a second vacuum attachment end for attachment to a vacuum line;

a vacuum line, the vacuum line having a first end and a second end, the first end being connected to the nipple receiving unit; and a vacuum source for creating a vacuum connected to the second end of the vacuum line, wherein the vacuum source is in vacuum communication with the nipple receiving end of the nipple receiving unit.

25. The method of claim 24, wherein the massaging element is a vibrating element.

26. The method of claim 24, wherein the massaging element delivers a peristaltic action, wherein the mammary gland is massaged from the chest wall to the nipple.

27. The method of claim 24, wherein the vacuum source is a syringe.

28. The method of claim 24, wherein the vacuum source is a vacuum pump.

29. The method of claim 24, wherein the vacuum source is a wall vacuum.

30. The method of claim 1, wherein the mammary gland fluid is a breast milk.

31. The method of claim 31, wherein the breast milk is a colostrum breast milk.

32. A method of determining the risk of breast cancer in a subject comprising:

quantifying the amount of a carotenoid in a biological sample obtained from a mammary gland compared to an amount of a carotenoid in a control sample, wherein if a ratio of carotenoids in the biological sample to the carotenoids in the control sample is less than one the ratio is indicative of a risk of breast cancer.

33. The method of claim 32, wherein the biological sample is a mammary fluid.

34. The method of claim 33, wherein the mammary fluid is colostrum breast milk.

35. The method of claim 32, wherein the control sample is a plasma sample from the same subject or a colostrum breast milk control.

36. The method of claim 32, wherein the subject is a mammal.

37. The method of claim 36, wherein the mammal is a human.

* * * * *

UNITED STATES PATENT AND TRADEMARK OFFICE
CERTIFICATE OF CORRECTION

PATENT NO.    : 6,471,660 B1
DATED         : October 29, 2002
INVENTOR(S)   : Chandice Covington It is certified that error appears in the above-identified patent and that said Letters Patent is hereby corrected as shown below:

<u>Title page,</u>
Item [73], the correct assignee is:

-- Wayne State University --

Signed and Sealed this

Fourth Day of February, 2003

JAMES E. ROGAN
*Director of the United States Patent and Trademark Office*